United States Patent [19]

Kato et al.

[11] Patent Number: 5,550,275
[45] Date of Patent: Aug. 27, 1996

[54] METHOD OF PREPARING DIARYLCHLOROPHOSPHATE

[75] Inventors: Mutsuno Kato; Yoshifusa Hara; Masao Takada, all of Tokyo, Japan

[73] Assignee: Nippon Chemical Industrial Co., Ltd., Tokyo, Japan

[21] Appl. No.: 335,345

[22] Filed: Nov. 3, 1994

[30] Foreign Application Priority Data

Nov. 8, 1993 [JP] Japan ..................... 5-278367

[51] Int. Cl.$^6$ ..................... C07F 9/14
[52] U.S. Cl. ..................... 558/140; 558/148
[58] Field of Search ..................... 558/140, 148

[56] References Cited

U.S. PATENT DOCUMENTS

| | | | |
|---|---|---|---|
| 3,696,176 | 10/1972 | Colby | 558/140 |
| 4,213,922 | 7/1980 | Maier | 558/140 |
| 4,845,261 | 7/1989 | Fuentes | 558/101 |
| 5,245,069 | 9/1993 | McManus | 558/148 |

FOREIGN PATENT DOCUMENTS

| | | |
|---|---|---|
| 1263748 | 3/1968 | Germany . |
| 3541627 | 5/1987 | Germany ..................... 558/140 |
| WO88/07046 | 9/1988 | WIPO . |

OTHER PUBLICATIONS

Chemical Abstracts, vol. 118, No. 24, AN 236420t, JP–5 001 084, Jan. 8, 1993.
Kosolapoff, G. M. et al. *Organic Phosphorus Compounds;* Wiley–Interscience: New York, 1973; pp. 309 and 513.

*Primary Examiner*—Johann Richter
*Assistant Examiner*—Michael G. Ambrose
*Attorney, Agent, or Firm*—Oblon, Spivak, McClelland, Maier & Neustadt, P.C.

[57] ABSTRACT

A method of preparing diarylchlorophosphate comprising the step of reacting alkyldiarylphosphate represented by formula (1) and thionyl chloride in the presence of a catalyst:

$$R^1O\text{---}P(O)(OAr)_2 \qquad (1)$$

(where $R^1$ represents an alkyl group having 1 to 4 carbon atoms, and Ar represents a substituted or unsubstituted aryl group). According to the invention there is provided a method of preparing diarylchlorophosphate having a high purity at a high yield, which can be advantageously used in industrial applications.

10 Claims, No Drawings

METHOD OF PREPARING DIARYLCHLOROPHOSPHATE

BACKGROUND OF THE INVENTION

1. Field of the Invention

The present invention relates to a method of preparing diarylchlorophosphate for use as an intermediate for medicines, agricultural chemicals, etc.

2. Discussion of the Background

Hitherto, diarylhalophosphate has been known as an organic phosphorus compound which may be used as an intermediate for medicines or agricultural chemicals, resin additive materials, or the like. Various methods for preparing diarylchlorophosphate have been disclosed including, for example, a method (1), disclosed in Japanese Patent Laid Open No. 2-503084 (KOHYO), in which alkyldiarylphosphate is halogenated using, for example, chlorine; and method (2), disclosed in Japanese Patent Laid Open No. 5-1084, in which alkyldiarylphosphate is reacted with phosphorus pentachloride.

However, in the aforementioned method (1), since the alkyldiarylphosphite contains trivalent phosphorus, it has poor stability, and may be oxidized. In addition, only solvents which do not react with halogens, such as carbon tetrachloride or chlorobenzene can be used. Thus, it cannot be advantageously used for industrial purposes.

In method (2), phosphorus pentachloride is a solid also having sublimating properties, which not only make it difficult to handle when reacted with alkyldiarylphosphate, but also give rise to such problems as the generation of impurities as a result of secondary reactions, etc.

To overcome such conventional problems as those described above, the present invention aims at providing a method of preparing diarylchlorophosphate having high purity at a high yield, which can be advantageously used for industrial purposes.

SUMMARY OF THE INVENTION

In view of the aforementioned conventional methods of preparation, the present inventors have conducted a variety of research and have arrived at the present invention based on the knowledge that diarylchlorophosphate having high purity at a high yield can be prepared by reacting alkyldiarylphosphate and thionyl chloride in the presence of a catalyst.

That is, the present invention provides a method of preparing diarylchlorophosphate comprising the step of reacting alkyldiarylphosphate represented by formula (1) and thionyl chloride in the presence of a catalyst:

$$R^1O\text{—}P(O)(OAr)_2 \quad (1)$$

(where $R^1$ represents an alkyl group having 1 to 4 carbon atoms, and Ar represents a substituted or unsubstituted aryl group).

Further, the present invention provides the method of preparing diarylchlorophosphate which further includes the step of purifying the obtained diarylchlorophosphate through crystallization by hydrocarbon solvents.

The present invention will hereunder be described in detail.

The reaction formula for preparing the diarylchlorophosphate of the present invention is represented by formula (2):

$$R^1O\text{—}P(O)(OAr)_2 + SOCl_2 \rightarrow (ArO)_2P(O)Cl + SO_2 + R^1Cl \quad (2)$$

(where $R^1$ represents an alkyl group having 1 to 4 carbon atoms, and Ar represents a substituted or unsubstituted aryl group).

In the present invention, while the alkyldiarylphosphate represented by formula (1) may be prepared by any method, it may be obtained, for example, by first reacting alkylalcohol and phosphorus oxychloride to produce alkyldichlorophosphate, and then reacting the alkyldichlorophosphate with phenols. The reactions are respectively represented by the following formulas:

$$R^1OH+P(O)Cl_3 \rightarrow R^1OP(O)Cl_2+HCl \uparrow R^1OP(O)Cl_2+2ArOH+ 2NaOH \rightarrow R^1O\text{—}P(O)(OAr)_2+2NaCl+2H_2O$$

(where $R^1$ represents an alkyl group having 1 to 4 carbon atoms such as a methyl group, an ethyl group, a propyl group, a butyl group, or an allyl group; and, Ar represents an aryl group such as a 2,4-dichlorophenyl group, a phenyl group, a cresyl group, or a xylenyl group).

Concrete examples of the catalysts which may be used in the present invention include quaternary ammonium salts such as tetra-n-butylammonium bromide; phosphonium salts such as tetra-n-butylphosphonium bromide; pyridinium salts such as ethylpyridinium bromide; amines such as triethyl and pyridine; phosphoric amides such as hexamethylphosphoric triamide; and, phosphines such as triphenyl phosphine.

In the reaction of the present invention, alkyldiarylphosphate and thionyl chloride are reacted by heat in the presence of any one of the aforementioned catalysts, which thereby accelerates the reaction.

The molar ratio of alkyldiarylphosphate and thionyl chloride is 1:1.1~1:5.0, and preferably 1:1.5~1:3. The amount of catalyst added is not particularly limited, but usually is 0.1 to 20 grams, and preferably 0.5 to 10 grams to 1 mole of alkyldiarylphosphate.

Though the reaction conditions depend on the catalysts and raw materials used, the reaction temperature is usually 80° to 150° C., and preferably 100° to 120° C.; the reaction time is usually 0.5 to 24 hours, and preferably 3 to 10 hours. After the reaction, cooling the resulting mixture produces an oily substance.

In the present invention, a powdered diarylchlorophosphate of high purity is obtained using hydrocarbon solvent or a mixed solvent of hydrocarbon solvent and halogenated hydrocarbon solvent to remove impurities such as unwashed onium salt or secondary products. The preferred solvent is hydrocarbon solvent. Usable hydrocarbon solvents include n-hexane and cyclohexane. Usable halogenated hydrocarbon solvents include methylenedichloride, chloroform, and tetrachloroethylene. The mixing ratio of the halogenated hydrocarbon solvent to the hydrocarbon solvent in weight percent is preferably 10~20% to 80~90%.

In one method of purification, any one of the aforementioned solvents can be used to dissolve a proper amount of diarylchlorophosphate therein by heating. The resulting mixture is cooled down to about 0° C. or less, which precipitates crystals. When the crystals, under an atmosphere of nitrogen, are filtered and separated, and dried, diarylchlorophosphate having a high purity is obtained.

EXAMPLES

The present invention will be hereunder described with reference to the examples.

Example 1

An 83.2 g (0.2 mol) sample of O-ethyl-O, O-bis(2,4-dichlorophenyl)phosphate was placed in a 200 ml rounded bottom flask with an agitator, a dropping funnel, a thermometer, and a cooler set therein. After 47.6 g (0.4 mol) of thionyl chloride was added thereto at room temperature, 1.0 g of pyridine was added dropwise to the resulting mixture. Thereafter, with its temperature increased to 100° C., the mixture was aged for 6 hours. Then, upon recovering excess thionyl chloride at 60° C. and at a pressure of 20 mmHg, 83.7 g of a yellow transparent liquid was obtained. The rough yield was 103.1%. Liquid chromatograph analysis revealed that the purity of O, O-bis(2,4-dichlorophenyl)chlorophosphate was 93.5%. The true yield obtained from O-ethyl-O, O-bis(2,4-dichlorophenyl)phosphate was 96.4%.

The obtained 93.5% pure O, O-bis(2,4-dichlorophenyl)chlorophosphate having a mass of 81.5 g was placed in the flask. Then, 70 ml of n-hexane was added thereto to dissolve the substance at 40° C. Upon cooling the resulting solution down to 0° C., white crystals were precipitated. Under an atmosphere of nitrogen, the precipitated crystals were filtered and separated, and dried to obtain 70.4 g of the white crystals. The purity of the white crystals was 98.8%, and the recovery due to crystallization was 86.4%.

Example 2

An 83.2 g (0.2 mol) sample of O-ethyl-O, O-bis(2,4-dichlorophenyl)phosphate was placed in a 200-ml rounded bottom flask with an agitator, a dropping funnel, a thermometer, and a cooler set therein. After 47.6 g (0.4 mol) of thionyl chloride was added dropwise thereto at room temperature, 1.0 g of tetra-n-butylphosphonium bromide was added to the resulting mixture. Thereafter, with its temperature increased to 100° C., the mixture was aged for 6 hours. Then, upon recovering excess thionyl chloride at 60° C. and at a pressure of 20 mmHg, 85.3 g of a yellow transparent liquid was obtained. The rough yield was 105.0%. Liquid chromatograph analysis revealed that the purity of O, O-bis(2,4-dichlorophenyl)chlorophosphate was 91.2%. The true yield obtained from O-ethyl-O, O-bis(2,4-dichlorophenyl)phosphate was 95.8%.

The obtained 91.2% pure O, O-bis(2,4-dichlorophenyl)chlorophosphate having a mass of 80 g was placed in the flask. Then, 70 ml of n-hexane was added to dissolve the substance at 40° C. Upon cooling the resulting solution down to 0° C., white crystals were precipitated. Under an atmosphere of nitrogen, the precipitated crystals were filtered and separated, and dried to produce 67.5 g of the white crystals. The purity of the white crystals was 98.0%, and the recovery due to crystallization was 84.4%.

Example 3

A 55.6 g (0.2 mol) sample of O-ethyl-O, O-diphenylphosphate was placed in a 200 ml rounded bottom flask with an agitator, a dropping funnel, a thermometer, and a cooler set therein. After 47.6 g of thionyl chloride was added dropwise at room temperature, 1.0 g of pyridine was added to the resulting mixture. Thereafter, with its temperature increased to 100° C., the mixture was aged for 4 hours. Then, upon recovering excess thionyl chloride at 60° C. and at a pressure of 20 mmHg, 55.1 g of a yellow transparent liquid was obtained. The rough yield was 102.6%. Liquid chromatograph analysis revealed that the purity of O, O-diphenylchlorophosphate was 94.4%. The true yield obtained from O-ethyl-O, O-diphenylphosphate was 96.9%.

The obtained 94.4% pure O, O-diphenylchlorophosphate having a mass of 50.0g was placed in the flask. Then, 70 ml of n-hexane was added to dissolve the substance at 40° C. Upon cooling the resulting solution down to 0° C., white crystals were precipitated. Under an atmosphere of nitrogen, the precipitated crystals were filtered and separated, and dried to obtain 43.7 g of the white crystals. The purity of the white crystals was 99.0%, and recovery due to crystallization was 87.4%.

Example 4

An 83.2 g (0.2 mol) sample of O-ethyl-O, O-bis(2,4-dichlorophenyl)phosphate was placed in a 200 ml rounded bottom flask with an agitator, a dropping funnel, a thermometer, and a cooler set therein. Then, 47.6 g (0.4 mol) of thionyl chloride was added dropwise thereto at room temperature, 1.0 g of triethylamine was added to the resulting mixture. Thereafter, with its temperature increased to 95° C., the mixture was aged for 8 hours. Next, upon recovery of excess thionyl chloride at 60° C. and under a pressure of 20 mmHg, a yellow transparent liquid was obtained. The rough yield was 101.9%. Liquid chromatograph analysis revealed that the purity was 92.5%. The true yield obtained from O-ethyl-O, O-bis(2,4-dichlorophenyl)phosphate was 94.3%.

The obtained 92.5% pure O, O-bis(2,4-dichlorophenyl)chlorophosphate having a mass of 80.0 g was placed in the flask. Then, 70 ml of n-hexane was added to dissolve the substance at 40° C. Upon cooling the resulting solution down to 0° C., white crystals were precipitated. Under an atmosphere of nitrogen, the precipitated crystals were filtered and separated, and dried to obtain 67.0 g of white crystals. The purity of the white crystals was 98.2%, and the recovery due to crystallization was 83.8%.

Example 5

An 83.2 g (0.2 mol) sample of O-ethyl-O, O-bis(2,4-dichlorophenyl)phosphate was placed in a 200 ml rounded bottom flask with an agitator, a dropping funnel, a thermometer, and a cooler set therein. Then, 47.6 g (0.4 mol) of thionyl chloride was added dropwise at room temperature, 1.0 g of tetra-n-butylammoniumbromide was added to the resulting mixture. Thereafter, with its temperature increased to 110° C., the mixture was aged for 5 hours. Next, upon recovery of excess thionyl chloride at 60° C. and at a pressure of 20 mmHg, 83.9 g of a yellow transparent liquid was obtained. The rough yield was 103.3%. Liquid chromatograph analysis revealed that the purity of O, O-bis(2,4-dichlorophenyl)chlorophosphate was 94.9%. The true yield obtained from O-ethyl-O, O-bis(2,4-dichlorophenyl)phosphate was 98.0%.

The obtained 94.9% pure O, O-bis(2,4-dichlorophenyl)chlorophosphate having a mass of 80.0 g was placed to the flask. Then, 70 ml of n-hexane was added to dissolve the substance at 40° C. Upon cooling the resulting solution down to 0° C., white crystals were precipitated. Under an atmosphere of nitrogen, the precipitated crystals were filtered and separated, and dried to obtain 70.6 g of white crystals. The purity of the white crystals was 99.0%, and the recovery due to crystallization was 88.3%.

Example 6

An 83.2 g (0.2 mol) sample of O-ethyl-O, O-bis(2,4-dichlorophenyl)phosphate was placed in a 200 ml rounded bottom flask with an agitator, a dropping funnel, a thermometer, and a cooler set therein. Then, after 47.6 g (0.4 mol) of thionyl chloride was added dropwise thereto at room temperature, 1.0 g of hexamethylphosphoric triamide was further added dropwise to the resulting mixture. Thereafter, with its temperature increased to 100° C., the mixture was aged for 7 hours. Next, upon recovery of excess thionyl chloride at 60° C. and at a pressure of 20 mmHg, 80.4 g of a yellow transparent liquid was obtained. The rough yield was 99.0%. Liquid chromatograph analysis revealed that the purity of O, O-bis(2,4-dichlorophenyl)chlorophosphate was 93.0%. The true yield obtained from O-ethyl-O, O-bis(2,4-dichlorophenyl)phosphate was 92.1%.

The obtained 93.0% pure O, O-bis(2,4-dichlorophenyl)chlorophosphate having a mass of 75.0 g was placed in the flask. Then, 70 ml of n-hexane was added to dissolve the substance at 40° C. Upon, cooling the resulting solution down to 0° C., white crystals were precipitated. Under an atmosphere of nitrogen, the precipitated crystals were filtered and separated, and dried to obtain 65.9 g of the white crystals. The purity of the white crystals was 97.6%, and the recovery due to crystallization was 87.9%.

Example 7

An 83.2 g (0.2 mol) sample of O-ethyl-O, O-bis(2,4-dichlorophenyl)phosphate was placed in a 200 ml rounded bottom flask with an agitator, a dropping funnel, a thermometer, and a cooler set therein. After 47.6 g (0.4 mol) of thionyl chloride was added dropwise thereto at room temperature, 1.0 g of triphenylphosphine was further added to the resulting mixture. Thereafter, with its temperature increased to 110° C., the mixture was aged for 5 hours. Then, upon recovery of excess thionyl chloride at 60° C. and at a pressure of 20 mmHg, 83.1 g of a yellow transparent liquid was obtained. The rough yield was 102.3%. Liquid chromatograph analysis revealed that the purity of O, O-bis(2, 4-dichlorophenyl)chlorophosphate was 95.2%. The true yield obtained from O-ethyl-O, O-bis(2,4-dichlorophenyl)phosphate was 97.4%.

The 95.2% pure O, O-bis(2,4-dichlorophenyl)chlorophosphate having a mass of 80.0 g was placed in the flask. Then, 70 ml of n-hexane was added to dissolve the substance at 40° C. Upon cooling the resulting solution down to 0° C., white crystals were precipitated. Under an atmosphere of nitrogen, the precipitated white crystals were filtered and separated, and dried to obtain 71.8 g of the white crystals. The purity of the white crystals was 98.4%, and the recovery due to crystallization was 89.8%.

Example 8

A 61.2 g (0.2 mol) sample of O-ethyl-O, O-bis(3-methylphenyl)phosphate was placed in a 200 ml rounded bottom flask with an agitator, a dropping funnel, a thermometer, and a cooler set therein. After 47.6 g (0.4 mol) of thionyl chloride was added dropwise thereto at room temperature, 1.0 g of pyridine was added dropwise to the resulting mixture. Thereafter, with its temperature increased to 100° C., the mixture was aged for 10 hours. Next, upon recovery of excess thionyl chloride at 60° C. and at a pressure of 20 mmHg, 62.8 g of a brownish red transparent liquid was obtained. The rough yield thereof was 105.9%. Liquid chromatograph analysis revealed that the purity of O, O-bis(3-methylphenyl) chlorophosphate was 90.1%. The true yield obtained from O-ethyl-O, O-bis(3-methylphenyl)phosphate was 95.4%.

Example 9

A 67.6 g (0.2 mol) sample of O-ethyl-O, O-bis(3-methoxyphenyl)phosphate was placed in a 200 ml rounded bottom flask with an agitator, a dropping funnel, a thermometer, and a cooler set therein. After 47.6 g (0.4 mol) of thionyl chloride was added dropwise thereto at room temperature, 1.0 g of pydridine was added dropwise to the resulting mixture. Thereafter, with its temperature increased to 100° C., the mixture was aged for 10 hours. Then, upon recovery of excess thionyl chloride at 60° C. and at a pressure of 20 mmHg, 69.4 g of a brownish red transparent liquid was obtained. The rough yield thereof was 105.6%. Liquid chromatograph analysis revealed that the purity of O, O-bis(3-methoxyphenyl) chlorophosphate was 91.0%. The true yield obtained from O-ethyl-O, O-bis(3-methoxyphenyl)phosphate was 96.1%.

Comparative Example 1

An 83.2 g (0.2 mol) sample of O-ethyl-O, O-bis(2,4-dichlorophenyl)phosphate was placed in a 200 ml rounded bottom flask with an agitator, a dropping funnel, a thermometer, and a cooler set therein. Then, 47.6 g (0.4 mol) of thionyl chloride was added dropwise thereto at room temperature. Thereafter, with its temperature increased to 100° C., the mixture was aged for 16 hours. During ripening the reacting liquid underwent liquid chromatograph analysis, which revealed that no O, O-bis(2,4-dichlorophenyl)chlorophosphate was produced.

Accordingly, the present invention provides a method for preparing diarylchlorophosphate having a high purity at a high yield, which can be advantageously used in industrial applications.

What is claimed is:

1. A method of preparing diarylchlorophosphate, which comprises:

a) reacting an alkyl diarylphosphate having the formula (I):

$$R^1O-P(O)(OAr)_2 \quad \text{(I)}$$

wherein $R^1$ is an alkyl group having 1 to 4 carbon atoms, and Ar represents aryl or substituted aryl; with thionyl chloride in the presence of a catalyst at a temperature from about 100° C. to 120° C.

2. The method of claim 1, which further comprises purifying the obtained diarylchlorophosphate by using hydrocarbon solvent or a mixed solvent of hydrocarbon and halogenated hydrocarbon for crystallization.

3. The method of claim 2, wherein hydrocarbon solvent is used for crystallization.

4. The method of claim 3, wherein said hydrocarbon solvent is n-hexane or cyclohexane.

5. The method of claim 1, wherein a mole ratio of alkyl diarylphosphate to thionyl chloride of about 1:1.1 to 1:5.0 is used.

6. The method of claim 1, wherein said aryl is phenyl.

7. The method of claim 1, wherein said substituted aryl is selected from the group consisting of 2,4-dichlorophenyl, cresyl and xylenyl.

8. The method of claim 1, wherein said catalyst is selected from the group consisting of quaternary ammonium salts, phosphonium salts, pyridinium salts, amines and phosphines.

9. The method of claim 8, wherein said catalyst is selected from the group consisting of tetra-n-butylammonium bromide, tetra-n-butylphosphonium bromide, ethylpyridinium bromide, triethylamine, pyridine, hexamethylphosphoric triamide and triphenylphosphine.

10. The method of claim 1, wherein said catalyst is used in an amount of 0.1 to 20 grams per mole of alkyldiarylphosphate.

* * * * *